United States Patent [19]
Figueroa et al.

[11] 3,970,392
[45] July 20, 1976

[54] ANALOG TO DIGITAL TO ANALOG STORAGE AND RETRIEVAL FOR A PLURALITY OF PHOTOMETRIC BLANKING VALUES

[75] Inventors: David Richard Figueroa, Pembroke Pines; Guenter Ginsberg, Miami, both of Fla.

[73] Assignee: Coulter Electronics, Inc., Hialeah, Fla.

[22] Filed: Oct. 17, 1974

[21] Appl. No.: 515,446

Related U.S. Application Data

[63] Continuation-in-part of Ser. No. 383,437, July 27, 1973.

[52] U.S. Cl. .............................. 356/179; 356/96; 356/180; 356/205
[51] Int. Cl.² .......................................... G01J 3/46
[58] Field of Search ............. 356/96, 97, 179, 205, 356/201, 180

[56] References Cited
UNITED STATES PATENTS

| 3,634,868 | 1/1972 | PeLavin et al. | 356/179 |
| 3,752,995 | 8/1973 | Liedholz | 356/205 |
| 3,829,221 | 8/1974 | deMendez et al. | 356/205 |
| 3,854,879 | 12/1974 | Figueroa et al. | 23/230 R |

*Primary Examiner*—Vincent P. McGraw
*Attorney, Agent, or Firm*—Silverman & Cass, Ltd.

[57] ABSTRACT

To enable the storage and retrieval of a plurality of different aliquot valves of blanking standards or serums for photometric comparison with plural test sample aliquots processed in a colorimeter of an automated chemistry system that does not contain a computer memory for its various operations, a blanking solution is fed into the system as if it was a test sample, plural aliquots of the blanking solution are taken and processed each with different reagents, the transmission of each processed blanking aliquot is converted to an analog measurement of absorbance and then converted into an equivalent digital value that is stored in a simple memory until subsequently needed. Thereafter, by an addressing of specific colorimetric measurements on then present test sample aliquots in the colorimeter, the blanking values are called from memory and converted back to their analog values for photometric comparison with the test sample aliquots.

7 Claims, 9 Drawing Figures

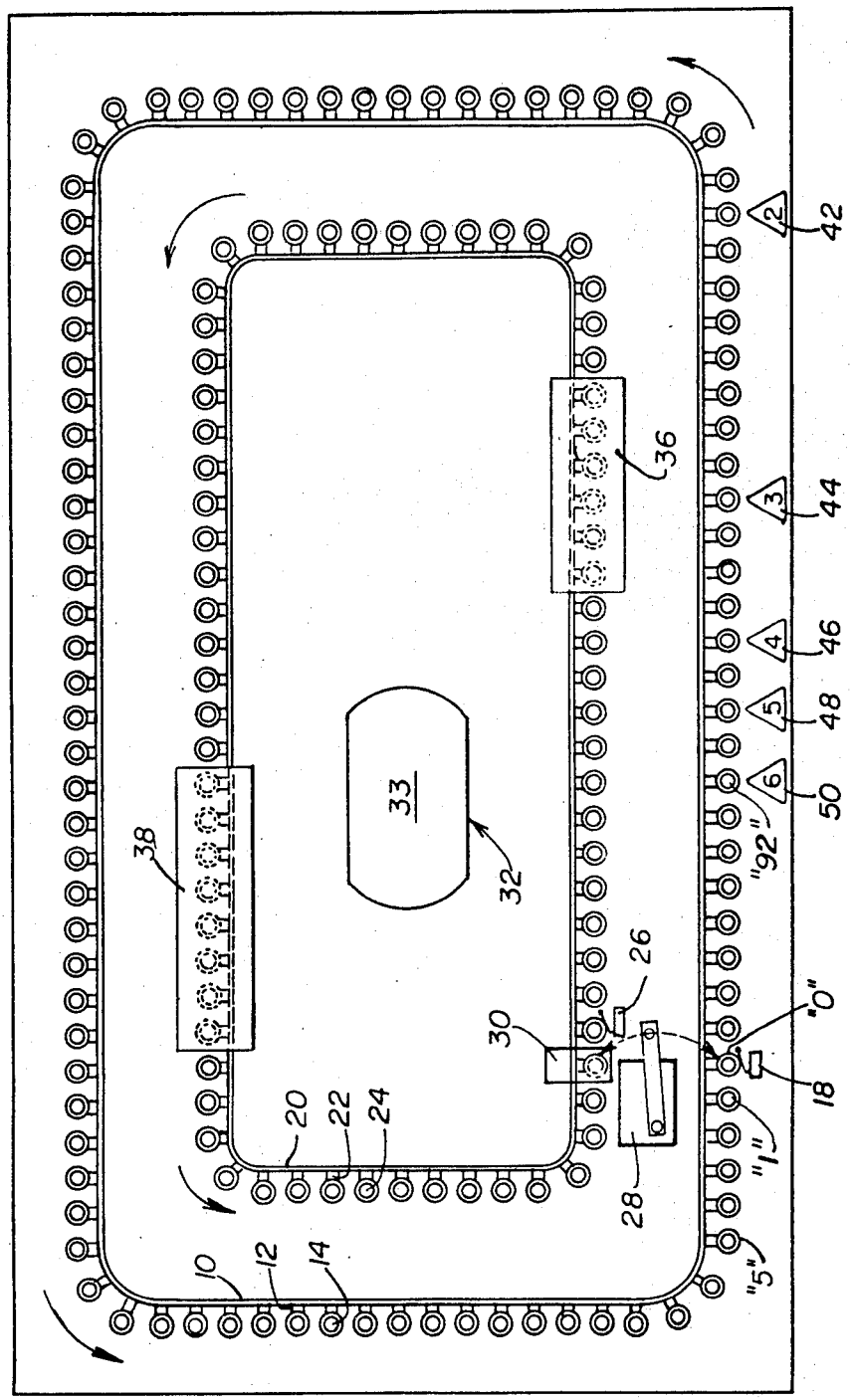

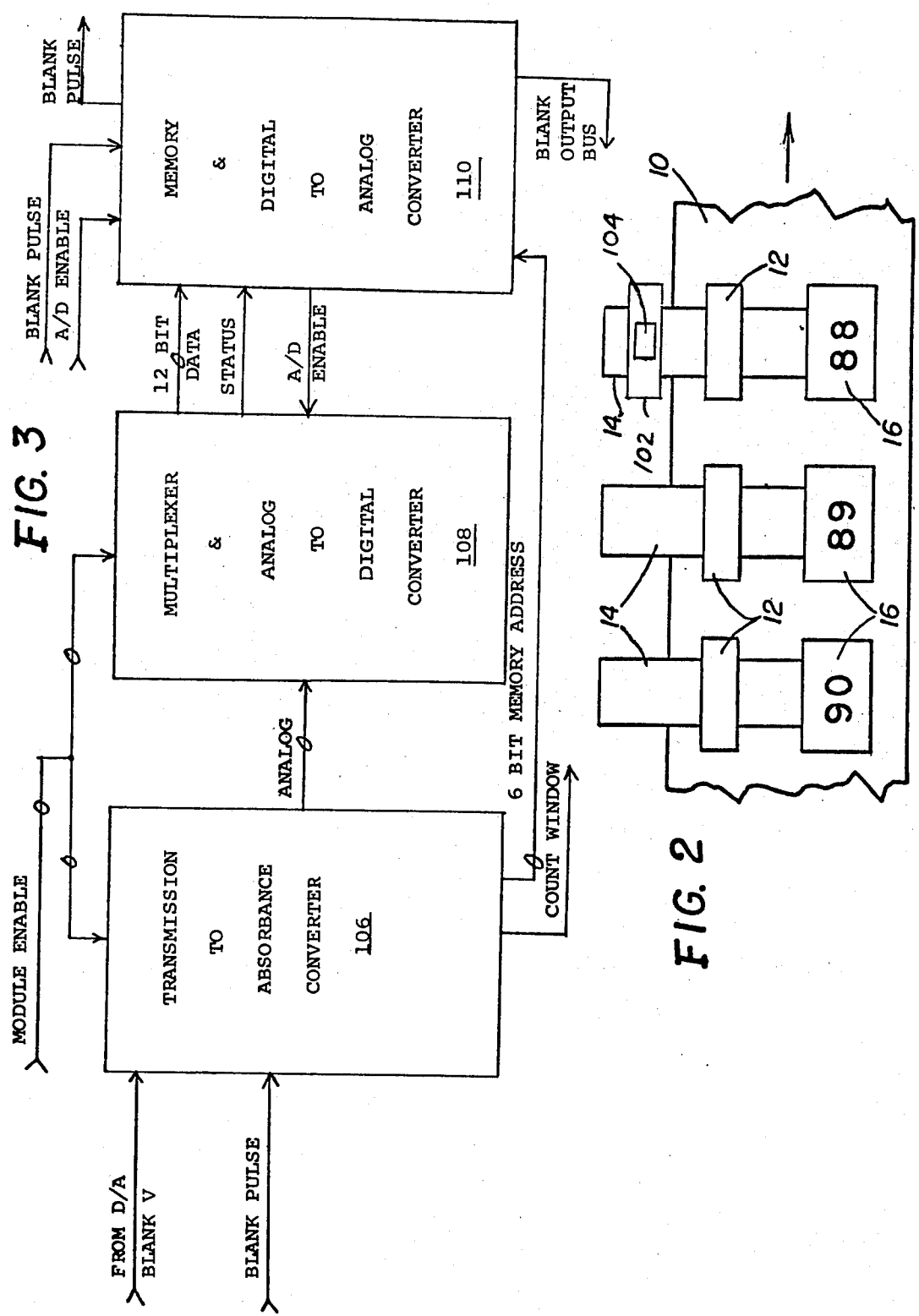

3,970,392

ANALOG TO DIGITAL TO ANALOG STORAGE AND RETRIEVAL FOR A PLURALITY OF PHOTOMETRIC BLANKING VALUES

CROSS REFERENCE TO RELATED APPLICATIONS AND PATENTS

This application is a Continuation-In-Part of our copending allowed application Ser. No. 383,437, filed July 27, 1973, now U.S. Pat. No. 3,854,879 entitled "Sample Identification and Test Data Correlation Method and Apparatus", such application hereby being incorporated herein by reference and being hereinafter referred to as the "parent" application.

Also incorporated by reference is application Ser. No. 341,069, filed Mar. 14, 1973, now U.S. Pat. No. 3,883,305 entitled "Improvements In Or Relating To Automatic Chemical Analysis Apparatus"; such application hereinafter being called the "basic" application and teaching apparatus for an automated chemistry system for which the present invention is especially well suited and a portion of which was improved by the invention in the "parent" application.

To the extent which may be necessary, the following two United States patents are incorporated by reference: 3,566,133 and 3,752,995. Patent 3,566,133 teaches voltage storage and rundown circuitry of the type used in the transmission to absorbance converter of the present invention. U.S. Pat. No. 3,752,995 teaches an analog blanking value storage improvement to the circuitry of patent 3,566,133.

BACKGROUND OF THE INVENTION

This invention generally relates to the storage of blanking values for photometric instruments and, more specifically, to the long term (relatively speaking) storage and then retrieval of a plurality of different blanking values for plural tests being accomplished in an automated chemistry system, such system not having a computer memory for storage of blanking values.

The need and use of blanking solutions, standards, comparison values, etc. for photometric instruments, such as commonly used in manual, semi-automatic and automated systems that analyze liquid and gas samples is well known in the art, as are the problems and limitations of existing blanking arrangements. U.S. Pat. No. 3,752,995 teaches an analog arrangement for storing only one blanking value for a relatively simple photometer. Complex and expensive automated chemistry systems normally contain a computer, the memory portion of which can be used for storage and retrieval of blanking values.

A problem arises when the photometric instrument or analysis system requires more than that conveniently provided by blanking storage according to U.S. Pat. No. 3,752,995 or the like but does not possess and cannot afford a computer.

SUMMARY OF THE INVENTION

The invention seeks to fill the void in the prior art by utilizing the test sample handling and processing portions of an automated chemistry system having no computer per se, by processing a blanking serum as if it was a test sample and thereby obtaining the several different absorbance values of the blanking serum which has been treated with different reagents etc. as if it had been a test sample. The absorbance values are obtained sequentially in analog form and are processed through a multiplexer and an analog to digital converter to obtain their digital values for easy storage in memory. During test sample processing, when a specific test colorimeter of the chemistry system is called upon, the associated address in the storage memory supplies its digital blanking value, which is reconverted to its analog value and fed to the colorimeter for comparison with the processed test aliquot according to the now well known voltage run down procedure. The storage memory is simple and inexpensive but retains the digital blanking values as long as desired.

BRIEF DESCRIPTION OF THE FIGURES

FIG. 1 is a top view of an automated chemistry system which includes apparatus according to the invention and is the same as FIG. 1 of the parent application incorporated herein by reference;

FIG. 2 is a front view of a portion of the sample conveyor and is the same as FIG. 2 of the parent application with the addition of a blanking cup identifier;

FIG. 3 is a block diagram of the three major electrical portions of the blanking arrangement according to the invention;

DESCRIPTION OF THE PREFERRED EMBODIMENT

Figure 4A:
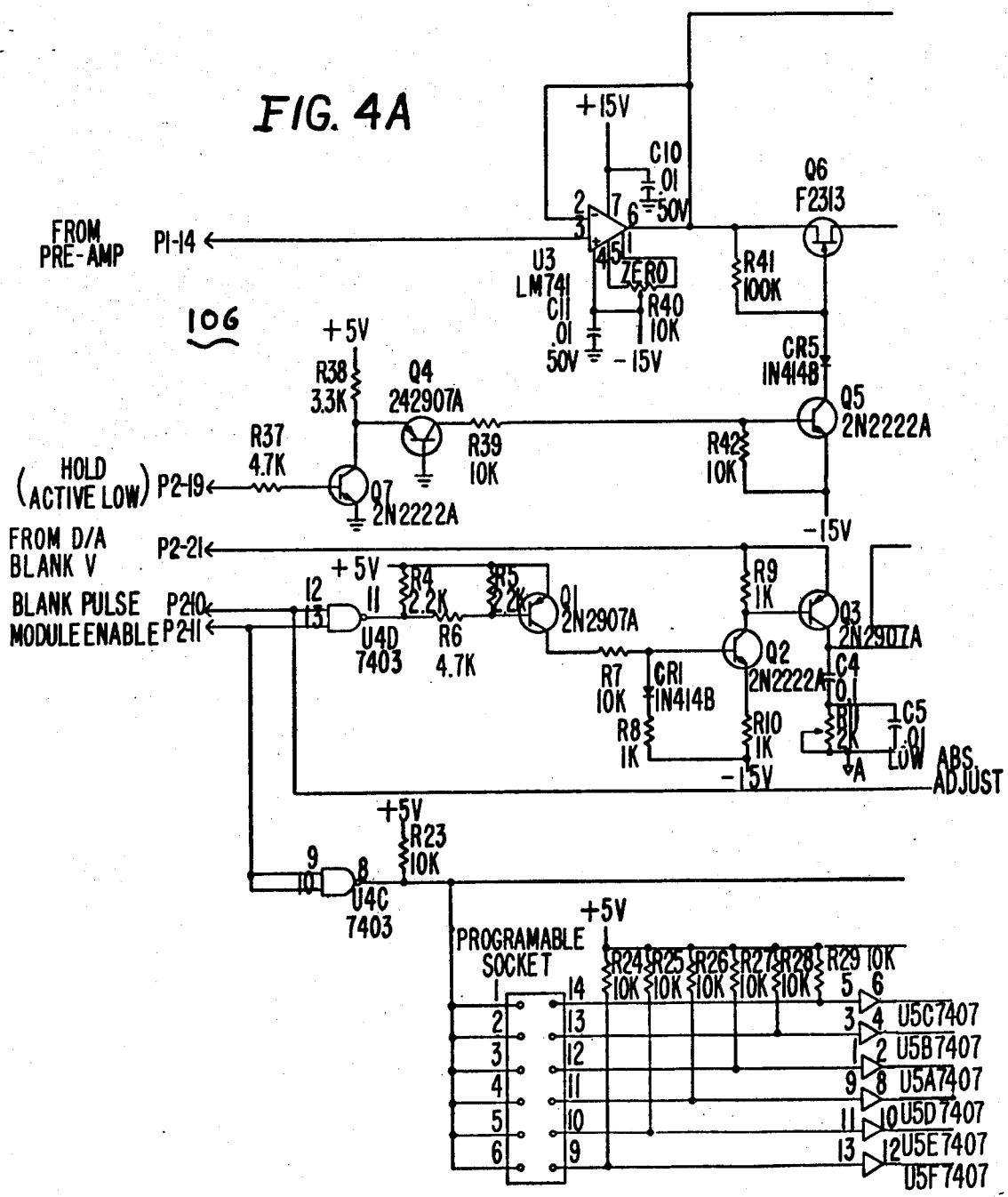
FIGS. 4A and 4B are the two halves of a detailed schematic of the Transmission to Absorbance Converter.

In view of the incorporation of both the cited parent and basic applications, the contentss and operation of the automated chemistry system and identification correlation apparatus will not be described hereinafter in detail even to the extent of discussing the elements and coaction pertinent to FIGS. 1 and 2 of this application. It is sufficient to contents that the testing station 38 contains a plurality, such as six, of colorimeters which require separate and different blanking, since each performs a photometric measurement of a different aliquot from different reactant tubes 24, all of which originated from a commont test sample tube 14 and are within the testing station 38 at the same time. The reactant tubes 24 passed through a reagent dispensing station 36, where they obtained different reagents, which were combined with the sample aliquot obtained at the receiving station 30.

The mechanical handling, fluid transferring and stepped transporting of a blanking serum and its aliquots according to the present invention is the same as for a test sample and its aliquots; such is part of the inventive concept which greatly reduces the complexity of the implementation of the invention. For the system to distinguish between a test sample in a sample tube or cup 14 and a blanking serum in the same type of tube 14, an indicator 102 is affixed to the tube 14 carrying the blanking serum, as shown in FIG. 2. Althoug the indicator could be of various types depending upon how the system was arranged to sense it, a simple form could be a collar slipped over the blanking serum tube. The collar 102 would have some form of detent 104, such as a cam surface, which would activate a simple switch (not illustrated) at one of the third datum points 42–50. Each of these third datum points 42–50 would include a switch similar to that illustrated at the transfer station 18. During any specific blanking procedure, only one of these switches would be activated, as would be determined by the test selector 34 (FIG. 3 of the parent application). If, for example, the five test sequence were to be programmed, the detent sensing switch at the datum point 48 would be activated by way of the console 33, such that when the tube 14 carrying the collar 102 passed the datum point 48, the cam surface 104 would trigger its switch.

As fully taught in the parent application, at the time that the sample tube reaches the third datum point, in this example the serum blanking tube reaching the datum point 48, its aliquots in fine sequential reactant tubes 24 will have passed through the reagent station 36, attain processng by suitable reagents and all be within the colormetric testing station 38. Accordingly, the triggering of the third datum point switch by the serum blanking indicator 102 signals the colorimeters, and next to be described circuitry, that five blanking aliquots are in the testing station and not five test aliquots.

As shown in FIG. 3 of this application, the blanking storage and retrieval arrangement comprises three interconnected circuit blocks each including a converter: a transmission to absorbance converter block 106. A multiplexer and analog to digital converter block 108, and a memory and digital to analog converter block 10.

Figure 4B:
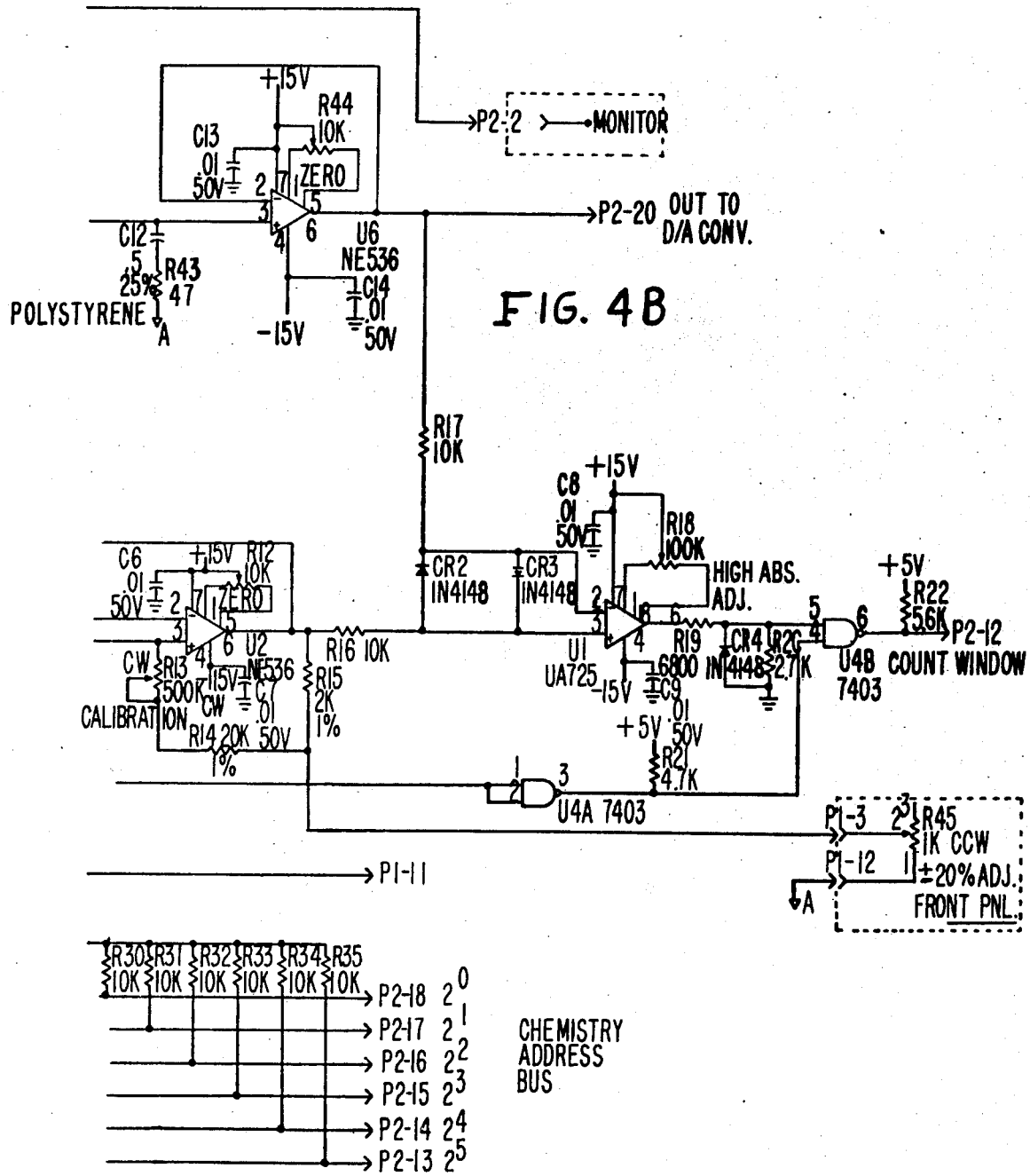
Figure 5A:
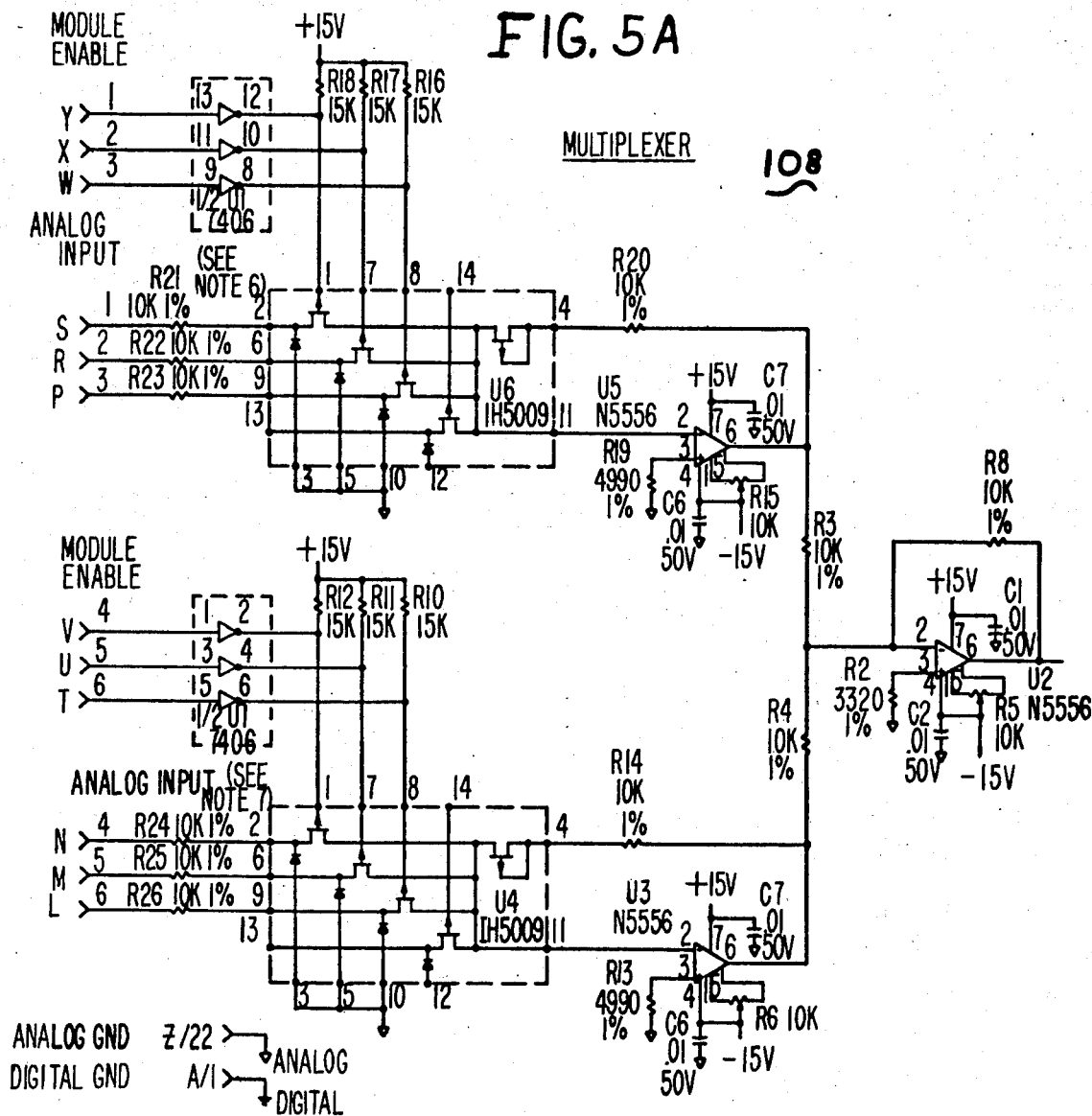
FIGS. 5A and 5B are the two halves of a detailed schematic of the Multiplexer and Analog to Digital Converter.

The transmission to absorbance converter 106 (T/A) comprises a plurality of similar modules equal in number to the number of colorimeters in the testing station 38, six in the present example. Once such T/A converter is detailed in FIGS. 4A and 4B in more than sufficient detail for one skilled in the art to build and operate same according to this invention. FIGS. 4A and 4B do not illustsrate the separate fluid transporting and photo-optical contents of each T/A converter module; such is taught in detail in the incorporate "basic" application. The fluid being supplied to the colorimeter, i.e. the test aliquot, or the blanking aliquot is photometrically monitored and generates a transmission representative analog signal. When the blanking serum indicator 102 (FIG. 2) activates the switch at a third datum point, such as 48, the T/A modules associated with that datum point (five of the six in this example) are enabled by a sequentially selecting input labeled "module enable" to transduce the absorbance of their blanking aliquot and feed same on an analog input line labeled "from pre-amp" from a preamplifier in the T/A module to appropriate analog inputs of the multiplexer portion of the block 108, shown in FIG. 5A, which also is coupled to the module enable input.

Figure 5B:
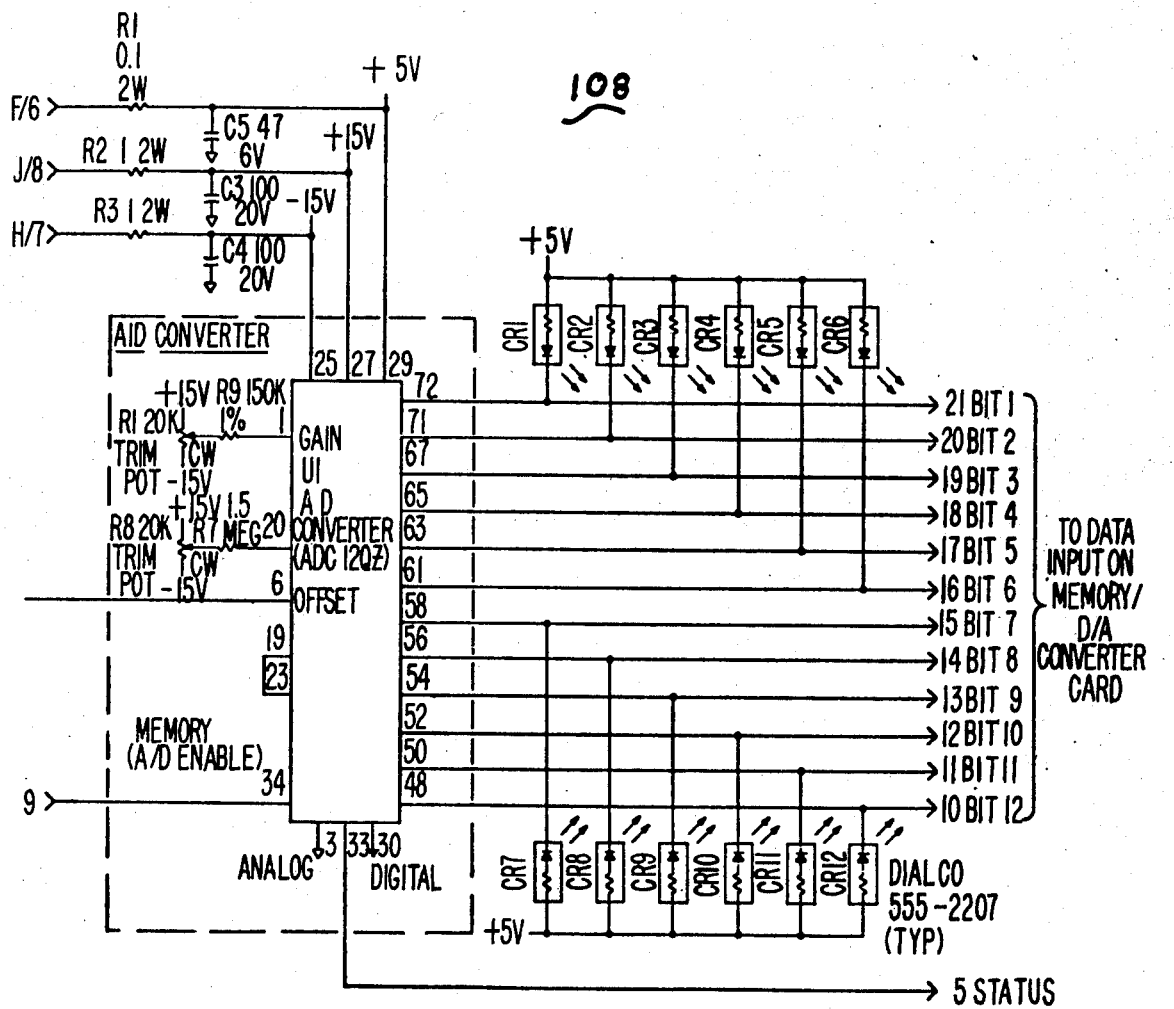
Figure 6A:
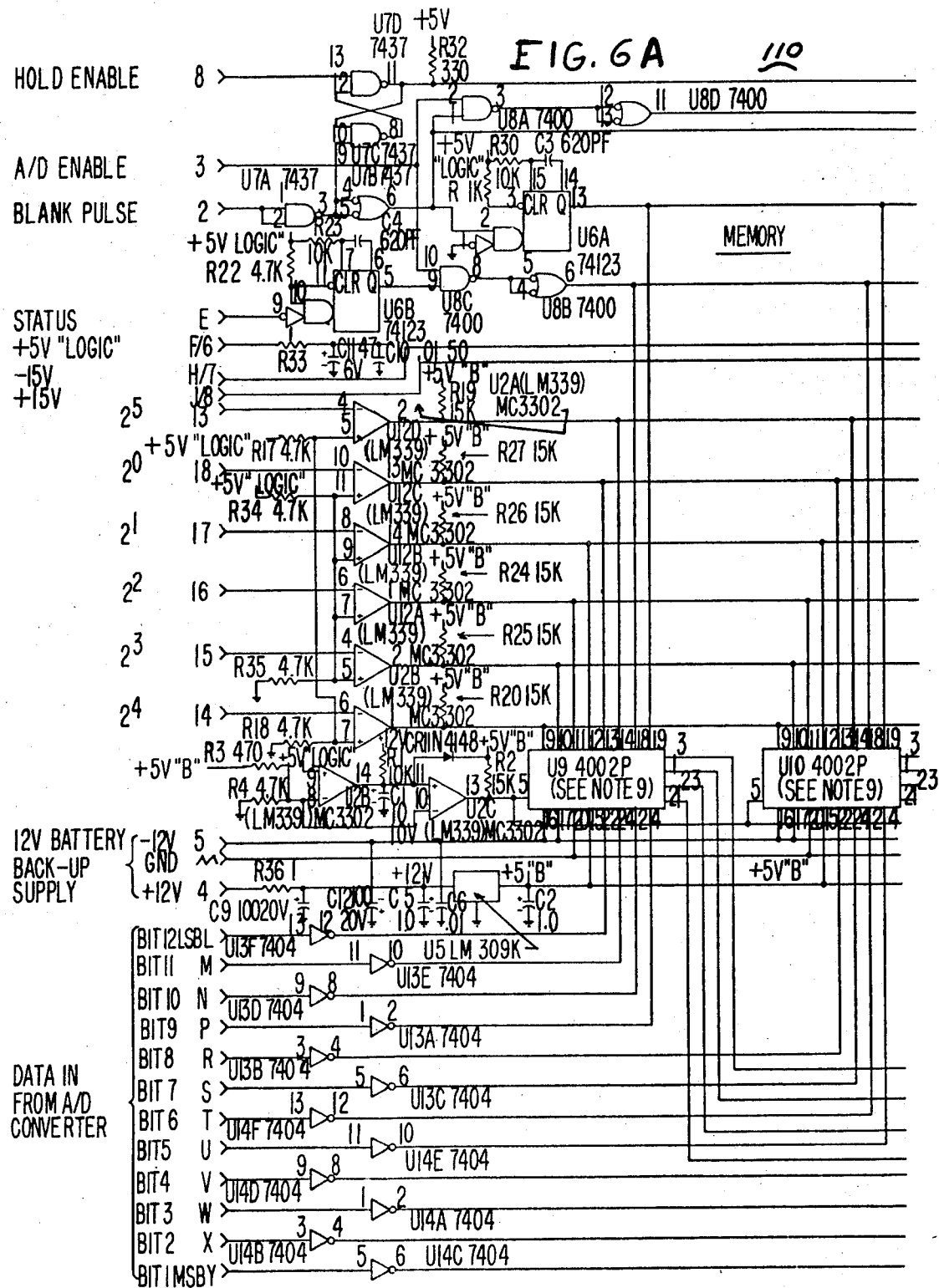
FIGS. 6A and 6B are the two halves of a detailed schematic of the Memory and Digital to Analog Converter.

The triggering of the third datum point switch by the indicator 102 also generates an "A/D enable" input in the memory and D/A converter block 110, seen at the top left of that block in both FIGS. 3 and 6A. The A/D enable input signal is fed through the converter block 110 and is coupled to the A/D converter in the converter block 108, as shown in detail in FIG. 5B, to enable same to receive and A/D convert the analog data coming from the T/A converter 106, The A/D converter illustrated in FIG. 5B has a twelve bit output for providing considerable resolution to the analog input absorbance values of the blanks.

Figure 6B:
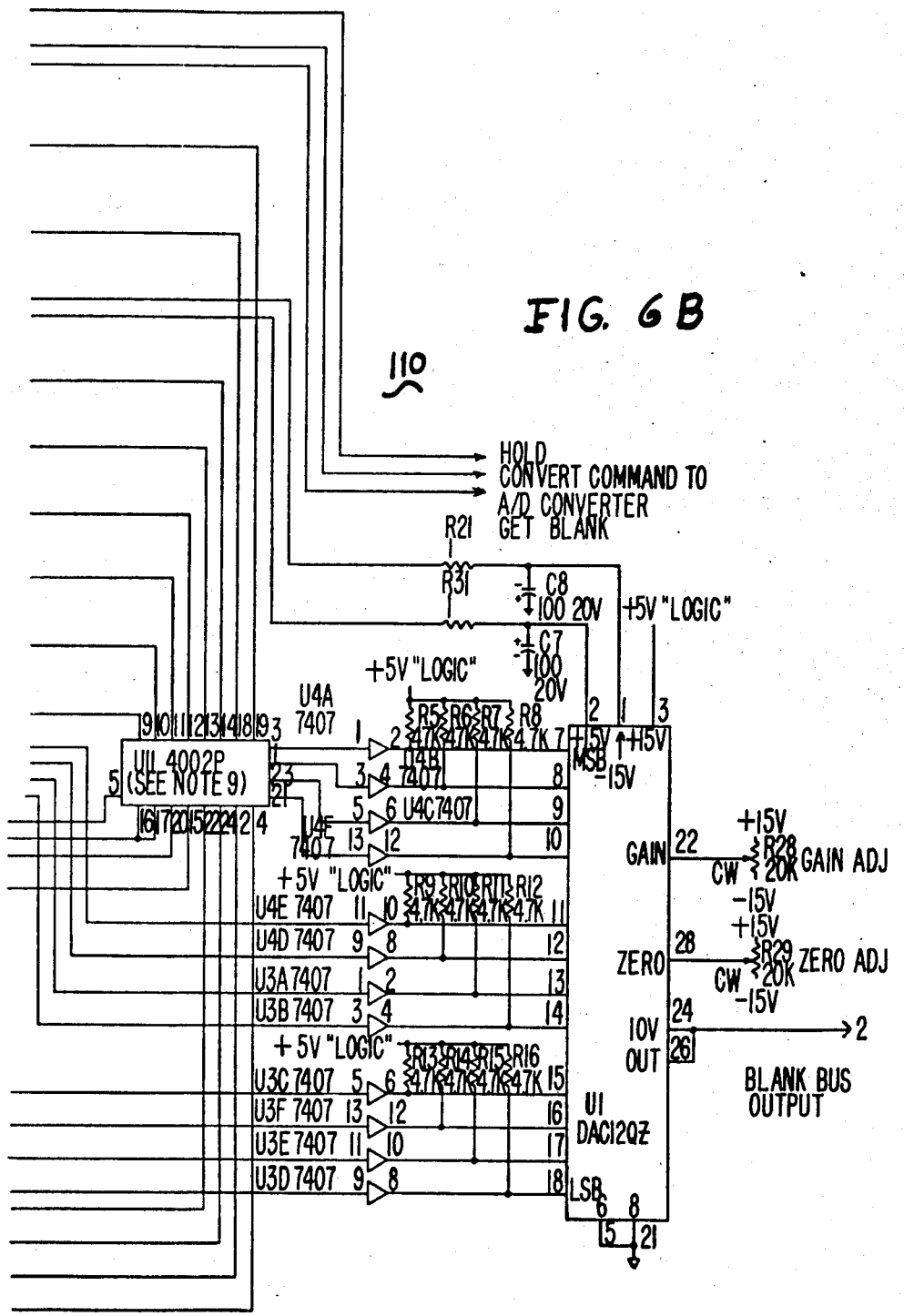

At the end of the twelve bit A/D conversion, the A/D converter generates a write enable signal on a "status" line coupled to the input of the memory portion shown in FIG. 6A. This status input is employed for enabling the memory elements which, as shown in FIGS. 6A and 6B, can be as simple as three memory chips each receiving a different four of the twelve digital bits from the A/D converter. The addressing of the memory locations in the memory is accomplished by way of the earlier described module enable signal which, in each T/A module 106, is fed to a programmable socket as illustrated in the lower portion of FIGS. 4A and 4B. Depending upon which T/A module is being enabled at any particular moment, there is a unique six bit address output from its programmable socket for identification of that T/A module. The six address bits are parallel coupled to the memory chips (see left end of FIG. 6A) for addressing each of the memory locations for each of the T/A modules. When addressed, the four bit positions of each of the three memory chips will be written into or read out, depending upon the then directed function. As above stated, all twelve bits comprise the stored blanking value and there are as many twelve bit words as there are stored blanks, with each work distinctly addressable with respect to one of the T/A modules. At this juncture it should be appreciated how the several different blanking values are obtained and stored.

Once the memory is loaded with the blanking values, the analyzing system is caused to operate, as taught in the basic and parent applications, for the processing of the test samples on the conveyor 10 and their aliquots on the conveyor 20. Additionally, as the test sample attains the third datum point (48 in this example) at which time its aliquots are in the colorimetric testing station 38, there is generated a "blank pulse" signal which activates the retrieval and D/A conversion of the specific blanking value for a specific T/A module. The blank pulse signal is fed into the memory and A/D converter 110 (see FIG. 6A top left corner) and is applied to the readout enable inputs of the memory chips. The blank pulse signal also is fed from the converter 110 to the converter 106 (left edge FIG. 4A) to enable all of its modules to receive the next to be provided data input. The earlier described module selection, memory addressing operations again are called upon, this time to steer the digitally stored twelve bit blanking values from the memory to the D/A converter (FIG. 6B) for conversion D/A and out from a "blank output bus" into the appropriate T/A module at an input labeled "from D/A blank V" (left edge FIG. 4A).

From this point in time forward, the selected T/A module operates as taught for example in U.S. Pat. No. 3,566,133 in a voltage run down measuring mode. The analog blanking value is first stored in a capacitor; then the test aliquot is transduced into an analog value that it employed as a comparison base. The stored blanking value is discharged until it equals the then being applied test aliquot value. The discharge duration is measured and converted into a data value representative of the transmission of the test aliquot. The "count window" output from the T/A converter (right edge FIG. 4B) is such an output.

Each of the T/A modules are enabled sequentially depending upon the then programmed test sequence, which controls the active third datum point location; until all of the programmed aliquots for one test sample have been tested. Thereupon, the cycle is repeated for the next following test sample and its aliquots. Except of course, the memory already has the needed blanking values.

At such time that different tests are to be accomplished or it is believed that due to elapsed time, temperature changes, etc., there has been a change in the then being used reagents, diluents, etc., such that a reblanking is necessary; the blank storing procedure is accomplished again with the insertion of a tube 14 with its collar 102 and suitable blanking serum From the above, taken in conjunction with the Figures and, to the extent necessary, the incorporated parent and basic applications, those skilled in the art will be capable of practicing the subject invention.

The schematics of FIGS. 4–6 show some circuitry not pertinent to the understanding of the present invention. For example a calibration mode which employs "hold" circuits and logic; and a backup battery supply.

Of course, the specifically illlustrated voltage run-down, module selecting, memory and memory addressing, circuitry, etc. are not to be considered limitations to the invention, variations to the schematics would be well within the skill of the art without departing from the spirit and scope of the invention as hereinafter claimed.

What is sought to be protected by United States Letters Patent is:

1. A storage and retrieval arrangement for a plurality of blanking values for use in a photometric system having a plurality of colorimeters which test a plurality of aliquots from a single test sample, said storage and retrieval arrangement comprising: means for distinguishing between the presentation of a blanking serum and a test sample to the photometric system, said distinguishing means generating a first signal to said arrangement to enable it to transduce blanking aliquots, as contrasted from test sample aliquots, and to provide an analog output for the absorbance value of each blanking aliquot; an analog to digital converter coupled to receive each said analog absorbance blanking value and enabled by said distinguishing means to convert same into a digital value; memory means coupled to receive and enabled by said distinguishing means to store each blanking aliquot digital value; memory addressing means responsive to which colorimeter is providing the analog blanking value for addressing said memory address location; a digital to analog converter coupled to receive as inputs the digital value stored in said memory and under control of said memory addressing means to feed same back to the correlated colorimeter for utilization at the time that such colorimeter is measuring a test sample aliquot.

2. A storage and retrieval arrangement according to claim 1 in which a multiplexer is interposed in front of said analog to digital converter for receipt of said analog blanking aliquot outputs, said multiplexer and said colorimeters being jointly coupled to control means for steering the analog outputs through said multiplexer.

3. A storage and retrieval arrangement according to claim 1 and in combination therewith voltage run down circuitry for receipt of both the retrieved analog blanking values and test aliquot values for comparison purposes.

4. A storage and retrieval arrangement according to claim 1 in which said distinguishing means includes mechanical means attached to a blanking serum carrier, and sensing means variably positionable along a path of movement of such carrier for sensing said mechanical means and initiating said first signal.

5. A storage and retrieval arrangment according to claim 4 further comprising programming means for selecting the number of blanking aliquots obtained from each blanking serum carrier and thereby determining the position of said sensing means such that said blanking serum carrier reaches said sensing position at the same time that its aliquots reach the colorimeters.

6. A storage and retrieval arrangement according to claim 1 in which said distinguishing means is arranged to generate a second signal when a test sample is being presented to the photometric systems, said second signal being coupled to said memory to initiate readout of its stored blanking values into said digital to analog converter.

7. A storage and retrieval arrangement according to claim 6 in which voltage run down circuitry is associated with each colorimeter, and said second signal is coupled to said voltage run down circuitry to enable receipt thereby of the feed back analog blanking values.

* * * * *

UNITED STATES PATENT AND TRADEMARK OFFICE
CERTIFICATE OF CORRECTION

PATENT NO. : 3,970,392

DATED : July 20, 1976

INVENTOR(S) : David R. Figueroa et al

It is certified that error appears in the above–identified patent and that said Letters Patent are hereby corrected as shown below:

Abstract, line 2, change "valves" to --values--. Column 2, line 2, after "in", insert --a--; line 37, change "contentss" to --contents--; line 42, change "contents" to --note--; line 47, change "commont" to --common--; line 63, change "althoug" to --although--. Column 3, line 15, change "fine" to --five--; line 17, change "processng" to --processing--; line 18, change "colormetric" to --colorimetric--; line 27, change ". A" to --, a--; line 29, change "10" to --110--; line 33, change "Once" to --One--; line 39, change "incorporate" to --incorporated--; line 62, change "," to --.--. Column 4, line 21, change "work" to --word--. Column 5, line 7, after "serum", insert --.--; line 44, after "memory", insert --and causing correlation of colorimeter to memory--.

Signed and Sealed this

Eighteenth Day of January 1977

[SEAL]

Attest:

RUTH C. MASON
Attesting Officer

C. MARSHALL DANN
Commissioner of Patents and Trademarks